US00PP08599P

United States Patent [19]

Resendez

[11] Patent Number: Plant 8,599

[45] Date of Patent: Feb. 15, 1994

[54] *LAGERSTROEMIA INDICA* CV. MONINK

[75] Inventor: Gilbert N. Resendez, La Verne, Calif.

[73] Assignee: Monrovia Nursery Company, Azusa, Calif.

[21] Appl. No.: 446

[22] Filed: Jan. 4, 1993

[51] Int. Cl.[5] ..... A01H 5/00
[52] U.S. Cl. ..... Plt./67.3
[58] Field of Search ..... Plt. 67.3

*Primary Examiner*—James R. Feyrer

[57] ABSTRACT

A new and distinct selection of Crape Myrtle shrub which shall be referred to hereinafter at *Lagerstroemia indica* cultivar Monink. *Lagerstroemia indica* cultivar Monink differs distinctively from other *Lagerstroemia indica* plants by its unique combination of a floriferous habit of rich pink flowers and a dwarf size and a more dense compact growth habit.

1 Drawing Sheet

BACKGROUND OF THE NEW PLANT

This invention relates to a new and distinct selection of *Lagerstroemia indica*, a member of the Lythraceae or Loosestrife family. *Lagerstroemia indica* cultivar Monink was discovered in a group of seedlings which originated from seed of *Lagerstroemia indica* 'Little Chief', seed was sown November 1983. During the summer of 1987, this new cultivar was selected at Monrovia Nurser Company, 18331 East Foothill Boulevard, Azusa, Calif. My new plant has been asexually reproduced by cuttings since 1987 at the above location in Azusa at Monrovia Nursery Company. The original seedlings displayed extreme variability, therefore the distinct phenotypic characteristics of my new selection that sets this plant apart from other *Lagerstroemia indica* plants would likely be lost through sexual reproduction. Therefore, sexual reproduction is prohibited and propagation is restricted to asexual reproduction by cuttings.

SUMMARY OF INVENTION

*Lagerstroemia indica* cv. Monink is unusual and unique in the dwarf growth habit. Normal *Lagerstroemia indica* is generally a tree achieving heights of 30 feet. The group of 'Petite' named *Lagerstroemia indica* will achieve heights of 15 feet. To date the largest *Lagerstroemia indica* 'Monink' is 3 feet tall by 3½ feet wide. My new selection should achieve a height of 5 feet and a spread of 5 feet.

*Lagerstroemia indica* cv. Monink is extremely floriferous. In the southern California region, blossoms appear from late May through late-November on plants which have been lightly trimmed to remove spent flowers.

Other *Lagerstroemia indica* selections that grow in the southern California area normally bloom from mid-July to mid-September.

Cold tolerance has not been tested in regions colder than 0° F. — the cold tolerant range for *Lagerstroemia indica* to which this cultivar is derived.

Therefore, it is assumed 0° F. is the lowest cold hardiness rating.

Tolerance or susceptibility to powdery mildew and aphids have not been observed as a problem in Azusa growing grounds. Susceptibility in other conditions has not been tested.

BRIEF DESCRIPTION OF DRAWINGS

The upper photograph exhibits a close-up of the flowers and demonstrates how the floriferous habit practically covers the plant when in bloom.

The lower photograph displays the overall dense compact growth habit.

BOTANICAL DESCRIPTION

Below is a detailed description of my new selection of *Lagerstroemia indica* cv. Monink, the color terminology is from The British Horticultural Color Charts.

Overall size and habit: Dwarf shrub, this plant does not exhibit a dominant leader. Primary branching occurs at the base of the plant above the crown. Secondary branches occur close together with a spacing of 1 cm to 2 cm range between branches. The internode length between leaves on the secondary branches range from 0.5 cm. to 1 cm. in length. After 5 years, the plant is expected to achieve a height of about 5 feet and a spread of 5 feet.

Branching: Strength and sturdiness appear strong upholding branches with terminal panicles in full bloom.

Flower habit: A 3 year old plant in July exhibits approximately 80% of the terminals with flower panicles. Eighty five panicles were counted on my selection which was 45 cm tall by 70 cm wide. In Southern California, flowers appear from late May through late November.

*Arrangement.*—Terminal panicles.

*Color.*—Petals — Persian Rose 628, slightly fading with age to Persian Rose 628/2. Cultivar Petite Pinkie is similar in color but possesses more pink color tones, Rhodamine Pink 527.

*Shape.*—Petals — The limb crinkly, the claw long and slender, Calyx-smooth and glabrous, lobes generally six.

*Size.*—Diameter — Ranging 2.5 cm to 3.5 cm, natural width — not pressed. Length of petal — Claw 1 cm. Limb 1 cm. Width of petal — Limb 1 - 1.5 cm.

Leaf:

Arrangement.—Opposite — Alternate on young growth, short-petioled.

*Size.*—Length varies 2.2 cm - 4 cm. Width varies 1.3 cm - 2 cm.

*Color.*—Above — Parsley green 00962/1. Underside — Spinach green 0960/2.

*Shape.*—Elliptic.

*Margins.*—Entire.

*Autumn color.*—Normal, not unusually colorful.

Bark: Color and texture are generally an identifying characteristic on Lagerstroemia, however, due to the dense shrubby habit, the bark is not visible.

Fruit: A woody capsule.

I claim:

1. A new and distinct variety of Lagerstroemia plant as substantially shown and described herein, that is characterized particularly as a novelty by the unique combination of a floriferous habit of rich pink flowers and a dwarf overall size and more dense compact growth habit.

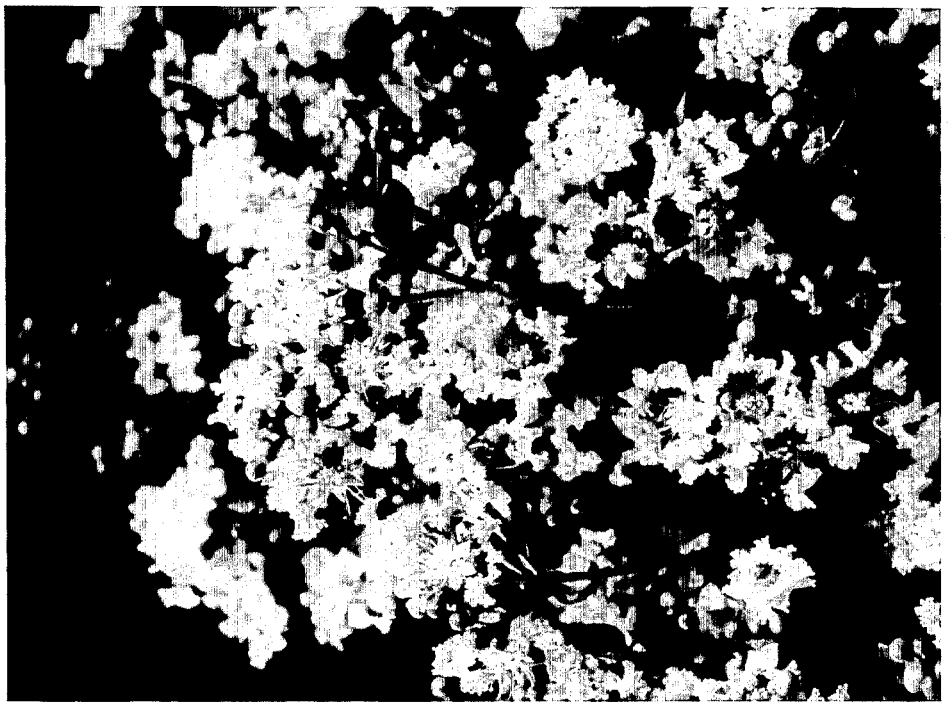
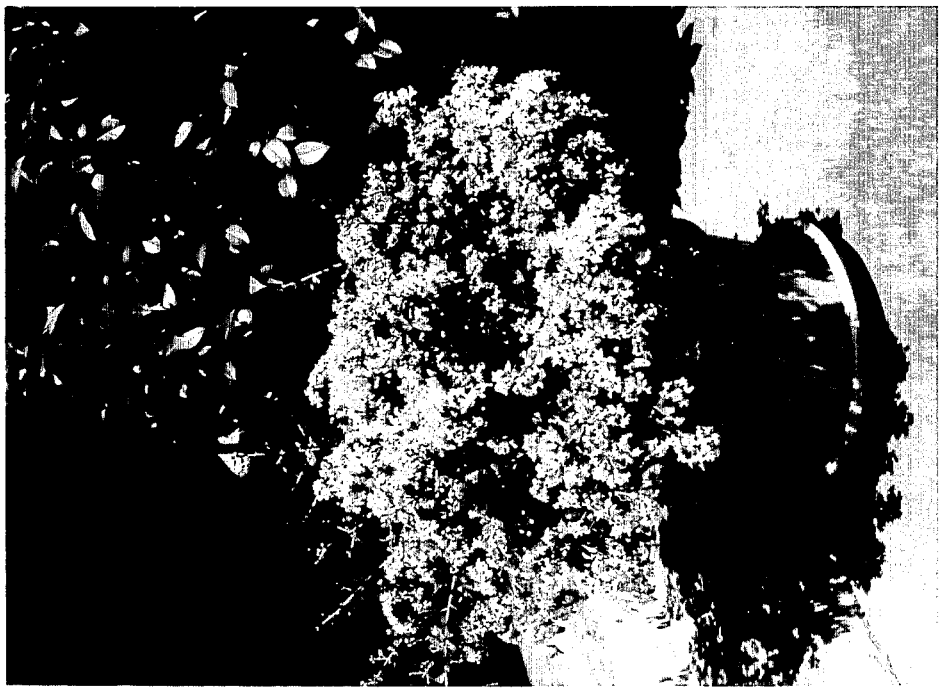

* * * * *